(12) United States Patent
Stone et al.

(10) Patent No.: US 7,608,098 B1
(45) Date of Patent: Oct. 27, 2009

(54) BONE FIXATION DEVICE

(75) Inventors: Kevin T Stone, Winona Lake, IN (US);
Jason D Meridew, Syracuse, IN (US);
Ryan A Kaiser, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 805 days.

(21) Appl. No.: 10/984,624

(22) Filed: Nov. 9, 2004

(51) Int. Cl.
*A61F 2/08* (2006.01)
*A61B 17/86* (2006.01)

(52) U.S. Cl. ...................................... 606/304

(58) Field of Classification Search ................. 606/151, 606/232, 300–30, 309; 623/11.11, 13.11–13.14
See application file for complete search history.

(56) References Cited

U.S. PATENT DOCUMENTS

| | | | |
|---|---|---|---|
| 26,501 A | 10/1859 | Kendrick et al. | |
| RE26,501 E | 12/1859 | Kendrick et al. | |
| 126,366 A | 4/1872 | Wills | |
| 233,475 A | 10/1880 | Cook et al. | |
| 261,501 A | 7/1882 | Vandermark | |
| 417,805 A | 12/1889 | Beaman | |
| 487,304 A | 12/1892 | Todd | |
| 837,767 A | 12/1906 | Aims | |
| 1,059,631 A | 4/1913 | Popovics | |
| 1,131,155 A | 3/1915 | Murphy | |
| 1,153,450 A | 9/1915 | Schaff | |
| 1,635,066 A | 7/1927 | Wells | |
| 2,012,776 A | 8/1935 | Roeder | |
| 2,065,659 A | 12/1936 | Cullen | |
| 2,108,206 A | 2/1938 | Meeker | |
| 2,242,003 A | 5/1941 | Lorenzo | |
| 2,302,986 A | 11/1942 | Vollrath | |
| RE22,857 E | 3/1947 | Ogburn | |
| 2,526,959 A | 10/1950 | Lorenzo | |
| 2,562,419 A | 7/1951 | Ferris | |
| 2,581,564 A | 1/1952 | Villegas | |
| 2,610,631 A | 9/1952 | Calicchio | |
| 2,669,774 A | 2/1954 | Mitchell | |
| 2,760,488 A | 8/1956 | Pierce | |
| 2,833,284 A | 5/1958 | Springer | |
| 2,846,712 A | 8/1958 | Markman | |
| 2,880,728 A | 4/1959 | Rights | |
| 2,881,762 A | 4/1959 | Lowrie | |
| 2,883,096 A | 4/1959 | Dawson | |
| 2,913,042 A | 11/1959 | Taylor | |

(Continued)

FOREIGN PATENT DOCUMENTS

AU  49572/64  3/1966

(Continued)

OTHER PUBLICATIONS

Arthrotek, A Biomet Company; Knees; Sure fire Hybrid Meniscal Device.

(Continued)

*Primary Examiner*—Anu Ramana
(74) *Attorney, Agent, or Firm*—Harness, Dickey

(57) ABSTRACT

A fixation device for securing tissue to a bone. The fixation device includes an anchor having a hollow body defining a longitudinal passage, and a plug configured to be received in at least a portion of the passage.

13 Claims, 5 Drawing Sheets

U.S. PATENT DOCUMENTS

| | | |
|---|---|---|
| 3,000,009 A | 9/1961 | Selstad |
| 3,013,559 A | 12/1961 | Thomas |
| 3,037,619 A | 6/1962 | Stevans |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,240,379 A | 3/1966 | Bremer et al. |
| 3,399,432 A | 9/1968 | Merser |
| 3,470,834 A | 10/1969 | Bone |
| 3,470,875 A | 10/1969 | Johnson |
| 3,500,820 A | 3/1970 | Almen |
| 3,515,132 A | 6/1970 | McKnight |
| 3,527,223 A | 9/1970 | Shein |
| 3,541,591 A | 11/1970 | Hoegerman |
| 3,547,389 A | 12/1970 | Mitchell |
| 3,579,831 A | 5/1971 | Stevens |
| 3,618,447 A | 11/1971 | Goins |
| 3,643,649 A | 2/1972 | Amato |
| 3,664,345 A | 5/1972 | Dabbs et al. |
| 3,675,639 A | 7/1972 | Cimber |
| 3,695,271 A | 10/1972 | Chodorow |
| 3,699,969 A | 10/1972 | Allen |
| 3,716,058 A | 2/1973 | Tanner, Jr. |
| 3,752,516 A | 8/1973 | Mumma |
| 3,757,629 A | 9/1973 | Schneider |
| 3,807,407 A | 4/1974 | Schweizer |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,907,442 A | 9/1975 | Reid |
| 3,910,281 A | 10/1975 | Kletschka et al. |
| 3,931,667 A | 1/1976 | Merser et al. |
| 3,943,932 A | 3/1976 | Woo |
| 3,946,740 A | 3/1976 | Bassett |
| 3,954,103 A | 5/1976 | Garcia-Roel et al. |
| 3,961,632 A | 6/1976 | Moossun |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,006,747 A | 2/1977 | Kronenthal et al. |
| 4,007,743 A | 2/1977 | Blake |
| 4,013,071 A | 3/1977 | Rosenberg et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,144,876 A | 3/1979 | DeLeo |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A * | 11/1979 | Herbert ............... 606/304 |
| 4,185,636 A | 1/1980 | Gabbay et al. |
| 4,196,883 A | 4/1980 | Einhorn et al. |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,275,717 A | 6/1981 | Bolesky |
| 4,287,807 A | 9/1981 | Pacharis et al. |
| 4,291,698 A | 9/1981 | Fuchs et al. |
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | DiFrancesco |
| 4,402,445 A | 9/1983 | Green |
| 4,409,974 A | 10/1983 | Freedland |
| 4,438,769 A | 3/1984 | Pratt et al. |
| 4,454,875 A | 6/1984 | Pratt et al. |
| 4,462,395 A | 7/1984 | Johnson |
| 4,463,753 A | 8/1984 | Gustilo |
| 4,484,570 A | 11/1984 | Sutter et al. |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,537,185 A | 8/1985 | Stednitz |
| 4,561,432 A | 12/1985 | Mazor |
| 4,570,623 A | 2/1986 | Ellison et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,653,487 A | 3/1987 | Maale |
| 4,653,489 A | 3/1987 | Tronzo |
| 4,662,068 A | 5/1987 | Polonsky |
| 4,667,675 A | 5/1987 | Davis |
| 4,669,473 A | 6/1987 | Richards et al. |
| 4,683,895 A | 8/1987 | Pohndorf |
| 4,705,040 A | 11/1987 | Mueller et al. |
| 4,716,893 A | 1/1988 | Fischer et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,738,255 A | 4/1988 | Goble et al. |
| 4,741,330 A | 5/1988 | Hayhurst |
| 4,741,336 A | 5/1988 | Failla et al. |
| 4,750,492 A | 6/1988 | Jacobs |
| 4,760,843 A | 8/1988 | Fischer et al. |
| 4,772,261 A | 9/1988 | Von Hoff et al. |
| 4,776,328 A | 10/1988 | Frey et al. |
| 4,781,190 A | 11/1988 | Lee |
| 4,784,126 A | 11/1988 | Hourahane et al. |
| 4,787,882 A | 11/1988 | Clarén |
| 4,790,297 A | 12/1988 | Luque |
| 4,809,695 A | 3/1989 | Gwathmey et al. |
| 4,823,794 A | 4/1989 | Pierce |
| 4,832,026 A | 5/1989 | Jones |
| 4,834,098 A | 5/1989 | Jones |
| 4,841,960 A | 6/1989 | Garner |
| 4,858,601 A * | 8/1989 | Glisson ............... 606/916 |
| 4,858,608 A | 8/1989 | McQuilkin |
| 4,860,513 A | 8/1989 | Whitman |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,901,721 A | 2/1990 | Hakki |
| 4,923,461 A | 5/1990 | Caspari et al. |

| | | | | | |
|---|---|---|---|---|---|
| 4,927,421 A | 5/1990 | Goble et al. | 5,447,512 A | 9/1995 | Wilson et al. |
| 4,946,468 A | 8/1990 | Li | 5,456,685 A | 10/1995 | Huebner |
| 4,950,285 A | 8/1990 | Wilk | 5,466,237 A | 11/1995 | Byrd, III et al. |
| 4,960,381 A | 10/1990 | Niznick | 5,467,786 A | 11/1995 | Allen et al. |
| 4,961,741 A | 10/1990 | Hayhurst | 5,470,334 A | 11/1995 | Ross et al. |
| 4,968,315 A | 11/1990 | Gatturna | 5,470,337 A | 11/1995 | Moss |
| 4,968,317 A | 11/1990 | Törmälä et al. | 5,474,572 A | 12/1995 | Hayhurst |
| 4,976,736 A | 12/1990 | White et al. | 5,484,442 A | 1/1996 | Melker et al. |
| 4,978,350 A | 12/1990 | Wagenknecht | 5,490,750 A | 2/1996 | Gundy |
| 4,983,176 A | 1/1991 | Cushman et al. | 5,496,331 A | 3/1996 | Xu et al. |
| 5,002,562 A | 3/1991 | Oberlander | 5,505,736 A | 4/1996 | Reimels et al. |
| 5,041,129 A | 8/1991 | Hayhurst et al. | 5,520,691 A | 5/1996 | Branch |
| 5,047,030 A | 9/1991 | Draenert | 5,522,820 A | 6/1996 | Caspari et al. |
| 5,053,046 A | 10/1991 | Janese | 5,522,846 A | 6/1996 | Bonutti |
| 5,053,047 A | 10/1991 | Yoon | 5,527,342 A | 6/1996 | Pietrzak et al. |
| 5,059,201 A | 10/1991 | Asnis | 5,527,343 A | 6/1996 | Bonutti |
| 5,059,206 A | 10/1991 | Winters | 5,545,178 A | 8/1996 | Kensey et al. |
| 5,084,050 A | 1/1992 | Draenert | 5,545,228 A | 8/1996 | Kambin |
| 5,084,058 A | 1/1992 | Li | 5,549,630 A | 8/1996 | Bonutti |
| 5,085,661 A | 2/1992 | Moss | 5,549,631 A | 8/1996 | Bonutti |
| 5,087,263 A | 2/1992 | Li | 5,571,139 A | 11/1996 | Jenkins, Jr. |
| 5,098,435 A | 3/1992 | Stednitz et al. | 5,573,286 A | 11/1996 | Rogozinski |
| 5,123,913 A | 6/1992 | Wilk et al. | 5,573,548 A | 11/1996 | Nazre et al. |
| 5,129,901 A | 7/1992 | Decoste | 5,584,862 A | 12/1996 | Bonutti |
| 5,129,904 A * | 7/1992 | Illi .................. 606/304 | 5,591,207 A | 1/1997 | Coleman |
| 5,139,499 A | 8/1992 | Small et al. | 5,593,407 A | 1/1997 | Reis |
| 5,143,498 A | 9/1992 | Whitman | 5,601,557 A | 2/1997 | Hayhurst |
| 5,149,329 A | 9/1992 | Richardson | 5,601,559 A | 2/1997 | Melker et al. |
| 5,152,790 A | 10/1992 | Rosenberg et al. | 5,601,571 A | 2/1997 | Moss |
| 5,154,189 A | 10/1992 | Oberlander | 5,641,256 A | 6/1997 | Gundy |
| 5,156,616 A | 10/1992 | Meadows et al. | 5,643,269 A | 7/1997 | Härle |
| 5,169,400 A | 12/1992 | Mühling et al. | 5,643,320 A | 7/1997 | Lower et al. |
| 5,176,682 A | 1/1993 | Chow | 5,645,546 A | 7/1997 | Fard |
| 5,178,629 A | 1/1993 | Kammerer | 5,645,547 A | 7/1997 | Coleman |
| 5,192,282 A | 3/1993 | Draenert | 5,647,874 A | 7/1997 | Hayhurst |
| 5,203,784 A | 4/1993 | Ross et al. | 5,658,289 A | 8/1997 | Boucher et al. |
| 5,203,787 A | 4/1993 | Noblitt et al. | 5,658,299 A | 8/1997 | Hart |
| 5,209,805 A | 5/1993 | Spraggins | 5,658,313 A | 8/1997 | Thal |
| 5,211,647 A | 5/1993 | Schmieding | 5,665,112 A | 9/1997 | Thal |
| 5,211,650 A | 5/1993 | Noda | 5,679,723 A * | 10/1997 | Cooper et al. ............... 523/115 |
| 5,214,987 A | 6/1993 | Fenton, Sr. | 5,683,419 A | 11/1997 | Thal |
| 5,242,447 A | 9/1993 | Borzone | 5,688,285 A | 11/1997 | Yamada |
| 5,249,899 A | 10/1993 | Wilson | 5,690,678 A | 11/1997 | Johnson |
| 5,258,015 A | 11/1993 | Li et al. | 5,695,497 A | 12/1997 | Stahelin |
| 5,269,160 A | 12/1993 | Wood | 5,697,929 A | 12/1997 | Mellinger |
| 5,269,783 A | 12/1993 | Sander | 5,702,397 A | 12/1997 | Goble et al. |
| 5,269,809 A | 12/1993 | Hayhurst et al. | 5,702,462 A | 12/1997 | Oberlander |
| 5,282,809 A | 2/1994 | Kammerer et al. | 5,707,373 A | 1/1998 | Sevrain et al. |
| 5,312,438 A | 5/1994 | Johnson | 5,713,904 A | 2/1998 | Errico et al. |
| 5,318,577 A | 6/1994 | Li | 5,716,359 A | 2/1998 | Ojima et al. |
| 5,318,578 A | 6/1994 | Hasson | 5,718,717 A | 2/1998 | Bonutti |
| 5,320,633 A | 6/1994 | Allen et al. | 5,720,765 A | 2/1998 | Thal |
| 5,334,204 A | 8/1994 | Clewett et al. | 5,725,549 A | 3/1998 | Lam |
| 5,336,229 A | 8/1994 | Noda | 5,725,556 A | 3/1998 | Moser et al. |
| 5,336,231 A | 8/1994 | Adair | 5,725,581 A | 3/1998 | Brånemark |
| 5,336,240 A | 8/1994 | Metzler et al. | 5,728,109 A | 3/1998 | Schulze et al. |
| 5,342,369 A | 8/1994 | Harryman, II | 5,728,136 A | 3/1998 | Thal |
| 5,358,511 A | 10/1994 | Gatturna et al. | 5,733,306 A | 3/1998 | Bonutti |
| 5,360,431 A | 11/1994 | Puno et al. | 5,743,912 A | 4/1998 | Lahille et al. |
| 5,364,400 A | 11/1994 | Rego, Jr. et al. | 5,746,754 A | 5/1998 | Chan |
| 5,374,268 A | 12/1994 | Sander | 5,749,898 A | 5/1998 | Schulze et al. |
| 5,383,878 A | 1/1995 | Roger et al. | 5,766,176 A | 6/1998 | Duncan |
| 5,391,171 A | 2/1995 | Schmieding | 5,769,899 A | 6/1998 | Schwartz et al. |
| RE34,871 E | 3/1995 | McGuire et al. | 5,776,196 A | 7/1998 | Matsuzaki et al. |
| 5,397,356 A | 3/1995 | Goble et al. | 5,782,864 A | 7/1998 | Lizardi |
| 5,403,348 A | 4/1995 | Bonutti | 5,792,142 A | 8/1998 | Galitzer |
| 5,417,691 A | 5/1995 | Hayhurst | 5,796,127 A | 8/1998 | Hayafuji et al. |
| 5,423,819 A | 6/1995 | Small et al. | 5,797,928 A | 8/1998 | Kogasaka |
| 5,425,766 A | 6/1995 | Bowald | 5,800,407 A | 9/1998 | Eldor |
| 5,433,751 A | 7/1995 | Christel et al. | 5,810,848 A | 9/1998 | Hayhurst |
| 5,437,680 A | 8/1995 | Yoon | 5,814,069 A | 9/1998 | Schulze et al. |
| 5,439,684 A | 8/1995 | Prewett et al. | 5,814,070 A | 9/1998 | Borzone et al. |
| 5,443,509 A | 8/1995 | Boucher et al. | 5,843,084 A | 12/1998 | Hart et al. |

| | | | | | | |
|---|---|---|---|---|---|---|
| 5,846,254 | A | 12/1998 | Schulze et al. | 6,319,271 | B1 | 11/2001 | Schwartz et al. |
| 5,860,973 | A | 1/1999 | Michelson | 6,328,758 | B1 | 12/2001 | Tornier et al. |
| 5,868,740 | A | 2/1999 | LeVeen et al. | 6,342,060 | B1 | 1/2002 | Adams |
| 5,871,484 | A | 2/1999 | Spievack et al. | 6,343,531 | B2 | 2/2002 | Amis |
| 5,871,486 | A | 2/1999 | Huebner et al. | 6,368,322 | B1 | 4/2002 | Luks et al. |
| 5,871,490 | A | 2/1999 | Schulze et al. | 6,368,326 | B1 | 4/2002 | Dakin et al. |
| 5,891,168 | A | 4/1999 | Thal | 6,379,361 | B1 | 4/2002 | Beck, Jr. et al. |
| 5,893,592 | A | 4/1999 | Schulze et al. | 6,383,199 | B2 | 5/2002 | Carter et al. |
| 5,895,395 | A | 4/1999 | Yeung | 6,387,113 | B1 | 5/2002 | Hawkins et al. |
| 5,897,564 | A | 4/1999 | Schulze et al. | 6,387,129 | B2 | 5/2002 | Rieser et al. |
| 5,899,902 | A | 5/1999 | Brown et al. | 6,398,785 | B2 | 6/2002 | Carchidi et al. |
| 5,941,439 | A | 8/1999 | Kammerer et al. | 6,409,743 | B1 | 6/2002 | Fenton, Jr. |
| 5,946,783 | A | 9/1999 | Plociennik et al. | 6,413,260 | B1 | 7/2002 | Berrevoets et al. |
| 5,948,002 | A | 9/1999 | Bonutti | 6,423,088 | B1 | 7/2002 | Fenton, Jr. |
| 5,951,560 | A | 9/1999 | Simon et al. | 6,428,562 | B2 | 8/2002 | Bonutti |
| 5,954,747 | A | 9/1999 | Clark | 6,432,123 | B2 | 8/2002 | Schwartz et al. |
| 5,961,524 | A | 10/1999 | Crombie | 6,440,136 | B1 | 8/2002 | Gambale et al. |
| 5,964,767 | A | 10/1999 | Tapia et al. | 6,454,768 | B1 | 9/2002 | Jackson |
| 5,964,783 | A | 10/1999 | Grafton et al. | 6,458,134 | B1 | 10/2002 | Songer et al. |
| 5,968,045 | A | 10/1999 | Frazier | 6,461,373 | B2 | 10/2002 | Wyman et al. |
| 5,968,047 | A | 10/1999 | Reed | 6,464,713 | B2 | 10/2002 | Bonutti |
| 5,976,127 | A | 11/1999 | Lax | 6,468,293 | B2 | 10/2002 | Bonutti et al. |
| 5,980,524 | A | 11/1999 | Justin et al. | 6,471,707 | B1 | 10/2002 | Miller et al. |
| 5,980,558 | A | 11/1999 | Wiley | 6,475,230 | B1 | 11/2002 | Bonutti et al. |
| 5,980,559 | A | 11/1999 | Bonutti | 6,497,901 | B1 | 12/2002 | Royer |
| 5,989,252 | A | 11/1999 | Fumex | 6,500,184 | B1 | 12/2002 | Chan et al. |
| 5,989,256 | A | 11/1999 | Kuslich et al. | 6,500,195 | B2 | 12/2002 | Bonutti |
| 5,997,542 | A | 12/1999 | Burke | RE37,963 | E | 1/2003 | Thai |
| 5,997,552 | A | 12/1999 | Person et al. | 6,508,820 | B2 | 1/2003 | Bales |
| 6,001,100 | A | 12/1999 | Sherman et al. | 6,508,821 | B1 | 1/2003 | Schwartz et al. |
| 6,010,525 | A | 1/2000 | Bonutti et al. | 6,511,498 | B1 | 1/2003 | Fumex |
| 6,016,727 | A | 1/2000 | Morgan | 6,517,542 | B1 | 2/2003 | Papay et al. |
| 6,022,352 | A | 2/2000 | Vandewalle | 6,517,579 | B1 | 2/2003 | Paulos et al. |
| 6,022,373 | A | 2/2000 | Li | 6,520,964 | B2 * | 2/2003 | Tallarida et al. ............... 606/71 |
| 6,024,758 | A | 2/2000 | Thal | 6,527,777 | B2 | 3/2003 | Justin |
| 6,039,753 | A | 3/2000 | Meislin | 6,527,794 | B1 | 3/2003 | McDevitt et al. |
| 6,045,574 | A | 4/2000 | Thal | 6,537,319 | B2 | 3/2003 | Whelan |
| 6,048,343 | A | 4/2000 | Mathis et al. | 6,540,770 | B1 | 4/2003 | Tornier et al. |
| 6,053,916 | A | 4/2000 | Moore | 6,547,564 | B1 | 4/2003 | Hansson |
| 6,068,648 | A | 5/2000 | Cole et al. | 6,551,343 | B1 | 4/2003 | Tormala et al. |
| 6,077,292 | A | 6/2000 | Bonutti | 6,554,830 | B1 | 4/2003 | Chappius |
| 6,096,060 | A | 8/2000 | Fitts et al. | 6,554,852 | B1 | 4/2003 | Oberlander |
| 6,117,160 | A | 9/2000 | Bonutti | 6,562,071 | B2 | 5/2003 | Järvinen |
| 6,117,162 | A | 9/2000 | Schmieding et al. | 6,565,572 | B2 | 5/2003 | Chappius |
| 6,123,710 | A | 9/2000 | Pinczewski et al. | 6,565,573 | B1 | 5/2003 | Ferrante et al. |
| 6,143,017 | A | 11/2000 | Thal | 6,569,187 | B1 | 5/2003 | Bonutti et al. |
| 6,149,653 | A | 11/2000 | Deslauriers | 6,572,655 | B1 | 6/2003 | Johnson |
| 6,149,669 | A | 11/2000 | Li | 6,585,740 | B2 | 7/2003 | Schlapfer et al. |
| 6,156,039 | A | 12/2000 | Thal | 6,589,245 | B1 | 7/2003 | Weiler et al. |
| 6,156,056 | A | 12/2000 | Kearns et al. | 6,607,548 | B2 | 8/2003 | Pohjonen et al. |
| 6,159,234 | A | 12/2000 | Bonutti et al. | 6,620,166 | B1 | 9/2003 | Wenstrom, Jr. et al. |
| 6,190,401 | B1 | 2/2001 | Green et al. | 6,620,195 | B2 | 9/2003 | Goble et al. |
| 6,190,411 | B1 | 2/2001 | Lo | 6,623,492 | B1 | 9/2003 | Berube et al. |
| 6,200,330 | B1 | 3/2001 | Benderev et al. | 6,623,524 | B2 | 9/2003 | Schmieding |
| 6,206,883 | B1 | 3/2001 | Tunc | 6,629,977 | B1 | 10/2003 | Wolf |
| 6,210,376 | B1 | 4/2001 | Grayson | 6,635,073 | B2 | 10/2003 | Bonutti |
| 6,214,012 | B1 | 4/2001 | Karpman et al. | 6,652,562 | B2 | 11/2003 | Collier et al. |
| 6,228,096 | B1 | 5/2001 | Marchand | 6,656,182 | B1 | 12/2003 | Hayhurst |
| 6,231,592 | B1 | 5/2001 | Bonutti et al. | 6,663,634 | B2 | 12/2003 | Ahrens et al. |
| 6,235,057 | B1 | 5/2001 | Roger et al. | 6,663,656 | B2 | 12/2003 | Schmieding et al. |
| 6,241,771 | B1 | 6/2001 | Gresser et al. | 6,666,868 | B2 | 12/2003 | Fallin |
| 6,245,081 | B1 | 6/2001 | Bowman et al. | 6,689,137 | B2 | 2/2004 | Reed |
| 6,258,091 | B1 | 7/2001 | Sevrain et al. | 6,712,849 | B2 | 3/2004 | Re et al. |
| 6,269,716 | B1 | 8/2001 | Amis | 6,716,957 | B2 | 4/2004 | Tunc |
| 6,270,518 | B1 | 8/2001 | Pedlick et al. | 6,726,722 | B2 | 4/2004 | Walkenhorst et al. |
| 6,273,890 | B1 | 8/2001 | Frazier | 6,746,483 | B1 | 6/2004 | Bojarski et al. |
| 6,283,973 | B1 | 9/2001 | Hubbard et al. | 6,755,836 | B1 | 6/2004 | Lewis |
| 6,287,325 | B1 | 9/2001 | Bonutti | 6,802,862 | B1 | 10/2004 | Roger et al. |
| 6,293,961 | B2 | 9/2001 | Schwartz et al. | 6,808,526 | B1 | 10/2004 | Magerl et al. |
| 6,299,615 | B1 | 10/2001 | Huebner | 6,814,741 | B2 | 11/2004 | Bowman et al. |
| 6,302,888 | B1 | 10/2001 | Mellinger et al. | 6,830,572 | B2 | 12/2004 | McDevitt et al. |
| 6,306,159 | B1 | 10/2001 | Schwartz et al. | 6,863,671 | B1 | 3/2005 | Strobel et al. |
| 6,312,448 | B1 | 11/2001 | Bonutti | 6,872,040 | B2 | 3/2005 | Deeg et al. |

| | | | | | |
|---|---|---|---|---|---|
| 6,875,216 B2 | 4/2005 | Wolf | DE | 3027138 | 12/1981 |
| 6,921,402 B2 | 7/2005 | Contiliano et al. | DE | 3225620 A1 | 2/1983 |
| 6,972,027 B2 | 12/2005 | Fallin et al. | DE | 3136083 | 3/1983 |
| 6,989,034 B2 | 1/2006 | Hammer et al. | DE | 233303 A1 | 2/1986 |
| 2001/0051816 A1 | 12/2001 | Enzerink et al. | DE | 4302397 | 7/1993 |
| 2002/0019649 A1 | 2/2002 | Sikora et al. | DE | 29621340 | 5/1998 |
| 2002/0058966 A1 | 5/2002 | Tormala et al. | DE | 19841252 | 3/2000 |
| 2002/0123752 A1 | 9/2002 | Schultheiss et al. | EP | 0 108 912 A2 | 5/1984 |
| 2002/0169452 A1 | 11/2002 | Tormala et al. | EP | 0 129 422 | 12/1984 |
| 2002/0169478 A1 | 11/2002 | Schwartz et al. | EP | 0 241 240 | 10/1987 |
| 2003/0032961 A1 | 2/2003 | Pelo et al. | EP | 0 260 970 A2 | 3/1988 |
| 2003/0033021 A1 | 2/2003 | Plouhar et al. | EP | 0 315 371 A2 | 5/1989 |
| 2003/0033022 A1 | 2/2003 | Plouhar et al. | EP | 0 415 915 | 3/1991 |
| 2003/0036797 A1 | 2/2003 | Malaviya et al. | EP | 0440991 | 8/1991 |
| 2003/0036801 A1 | 2/2003 | Schwartz et al. | EP | 0441065 | 8/1991 |
| 2003/0078617 A1 | 4/2003 | Schwartz et al. | EP | 0 490 417 A1 | 6/1992 |
| 2003/0083662 A1 | 5/2003 | Middleton | EP | 0 598 219 A2 | 5/1994 |
| 2003/0088251 A1 | 5/2003 | Braun et al. | EP | 0651979 | 5/1995 |
| 2003/0105477 A1 | 6/2003 | Schwartz et al. | EP | 0669110 | 8/1995 |
| 2003/0130694 A1 | 7/2003 | Bojarski et al. | EP | 0686373 | 12/1995 |
| 2003/0135214 A1 | 7/2003 | Fetto et al. | EP | 0775473 | 5/1997 |
| 2003/0152522 A1 | 8/2003 | Miller et al. | EP | 0 913 123 A1 | 5/1999 |
| 2003/0167072 A1 | 9/2003 | Oberlander | EP | 0913131 | 5/1999 |
| 2003/0225459 A1 | 12/2003 | Hammer et al. | EP | 99121052.7 | 10/1999 |
| 2004/0002734 A1 | 1/2004 | Fallin et al. | EP | 99121106 | 10/1999 |
| 2004/0006345 A1 | 1/2004 | Vlahos et al. | EP | 1 013 229 A2 | 6/2000 |
| 2004/0006346 A1 | 1/2004 | Holmen et al. | EP | 1093773 | 4/2001 |
| 2004/0015172 A1 | 1/2004 | Biedermann et al. | EP | 1093774 | 4/2001 |
| 2004/0024456 A1 | 2/2004 | Brown, Jr. et al. | FR | 2622790 | 12/1989 |
| 2004/0087981 A1 | 5/2004 | Berube et al. | FR | 2688689 | 9/1993 |
| 2004/0122431 A1 | 6/2004 | Biedermann et al. | FR | 2717070 | 9/1995 |
| 2004/0138664 A1 | 7/2004 | Bowman | FR | 2744010 | 8/1997 |
| 2004/0138704 A1 | 7/2004 | Gambale et al. | FR | 2745999 | 9/1997 |
| 2004/0143344 A1 | 7/2004 | Malaviya et al. | FR | 2770764 | 5/1999 |
| 2004/0153103 A1 | 8/2004 | Schwartz et al. | GB | 2 083 751 | 3/1982 |
| 2004/0166169 A1 | 8/2004 | Malaviya | GB | 2 118 474 | 11/1983 |
| 2004/0220574 A1 | 11/2004 | Pelo et al. | GB | 2312376 | 10/1997 |
| 2004/0225292 A1 | 11/2004 | Sasso et al. | JP | 5362911 | 5/1978 |
| 2004/0243139 A1 | 12/2004 | Lewis et al. | JP | 5362912 | 5/1978 |
| 2004/0267164 A1 | 12/2004 | Rhodes et al. | JP | 5374942 | 6/1978 |
| 2004/0267265 A1 | 12/2004 | Kyle | JP | 5378230 | 6/1978 |
| 2004/0267270 A1 | 12/2004 | Jacobs et al. | JP | 54-166092 | 11/1979 |
| 2004/0267276 A1 | 12/2004 | Camino et al. | JP | 54-166093 | 11/1979 |
| 2004/0267277 A1 | 12/2004 | Zannis et al. | JP | 54-176284 | 12/1979 |
| 2004/0267304 A1 | 12/2004 | Zannis et al. | JP | 54-178988 | 12/1979 |
| 2005/0027307 A1 | 2/2005 | Schwartz et al. | JP | 62-159647 | 7/1987 |
| 2005/0033363 A1 | 2/2005 | Bojarski et al. | JP | 62-295657 | 12/1987 |
| 2005/0074495 A1 | 4/2005 | Schwartz et al. | JP | 5269160 | 10/1993 |
| 2005/0090828 A1 | 4/2005 | Alford | JP | 7-51292 | 2/1995 |
| 2005/0125073 A1 | 6/2005 | Orban et al. | JP | 10-211213 | 8/1998 |
| 2005/0137600 A1 | 6/2005 | Jacobs et al. | WO | WO 83/00615 | 3/1983 |
| 2005/0149033 A1 | 7/2005 | McGuire et al. | WO | WO 86/03666 | 12/1986 |
| 2005/0159812 A1 | 7/2005 | Dinger, III et al. | WO | WO 87/01270 | 3/1987 |
| 2005/0165482 A1 | 7/2005 | Goldhahn et al. | WO | WO 89/10096 | 11/1989 |
| 2006/0030948 A1 | 2/2006 | Manrique et al. | WO | EP 0502698 | 9/1992 |
| 2006/0167482 A1 | 7/2006 | Swain et al. | WO | WO 93/15694 | 8/1993 |
| 2006/0293709 A1 | 12/2006 | Bojarski et al. | WO | WO 97/37603 | 10/1997 |
| 2007/0055255 A1 | 3/2007 | Siegel | WO | WO 98/22047 | 5/1998 |
| 2007/0078435 A1 | 4/2007 | Stone et al. | WO | WO 98/22048 | 5/1998 |
| 2007/0083236 A1 | 4/2007 | Sikora et al. | WO | WO-9822048 | 5/1998 |
| | | | WO | WO 99/01084 | 7/1998 |
| FOREIGN PATENT DOCUMENTS | | | WO | WO 99/12480 | 9/1998 |
| AU | 4402/66 | 10/1967 | WO | WO-9901084 | 1/1999 |
| AU | 22237/67 | 11/1968 | WO | WO 99/44544 | 9/1999 |
| AU | 50285/69 | 8/1970 | WO | WO 00/40159 | 7/2000 |
| AU | 58504/69 | 1/1971 | WO | WO 01/39671 A1 | 11/2000 |
| AU | 59638/69 | 2/1971 | WO | WO 02/36020 A1 | 10/2001 |
| AU | 15054/70 | 11/1971 | WO | WO 03/071962 A2 | 9/2003 |
| AU | 36151/71 | 5/1973 | WO | WO 03/077772 A1 | 9/2003 |
| AU | 43812/68 | 9/1973 | | | |
| AU | A-71108/87 | 10/1987 | | | |
| DE | 2919009 C2 | 11/1979 | | | |

| | | |
|---|---|---|
| WO | WO 2005/104992 | 11/2005 |

OTHER PUBLICATIONS

A. Wieler, et al; Biodegradierbare Interferenzschrauben in der Kreuzbandchirurgie; OP-Journal 14 pp. 278-284; 1998.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com.; 2003.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

US 6,238,418, 05/2001, Schwartz et al. (withdrawn)

* cited by examiner

BONE FIXATION DEVICE

INTRODUCTION

Various methods of attaching tissue, such as sift tissue, grafts or ligaments to bone are known. In anterior cruciate ligament reconstruction (ACL), for example, interference screws can be used to secure the graft against the walls of tunnels drilled in the tibia and the femur. The interference screws are wedged between the graft and a wall of the tunnel. To facilitate insertion and improve anchoring, some interference screws include cutting threads or other anchoring features.

SUMMARY

The present teachings provide a fixation device for securing tissue to a bone. The fixation device includes an anchor having a hollow body defining a longitudinal passage, and a plug configured to be received in at least a portion of the passage.

The present teachings provide a method for securing tissue to a bone. The method includes forming a tunnel in a bone, passing the tissue through the tunnel, providing a cannulated anchor defining a longitudinal passage, inserting the anchor between the tissue and the tunnel, and plugging the longitudinal passage of the cannulated anchor.

Further areas of applicability of the present invention will become apparent from the detailed description provided hereinafter. It should be understood that the detailed description and specific examples, while indicating various aspects of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, although the devices and methods of the invention are illustrated for use in anterior cruciate ligament reconstruction (ACL) in knee surgery, use for securing any soft tissue, hard tissue, bone cartilage, ligament, natural or artificial graft, such as, for example, polylactide (PLA), polyglolide (PGA), polyurethane urea, and other grafts, to a bone is contemplated.

Figure 1:
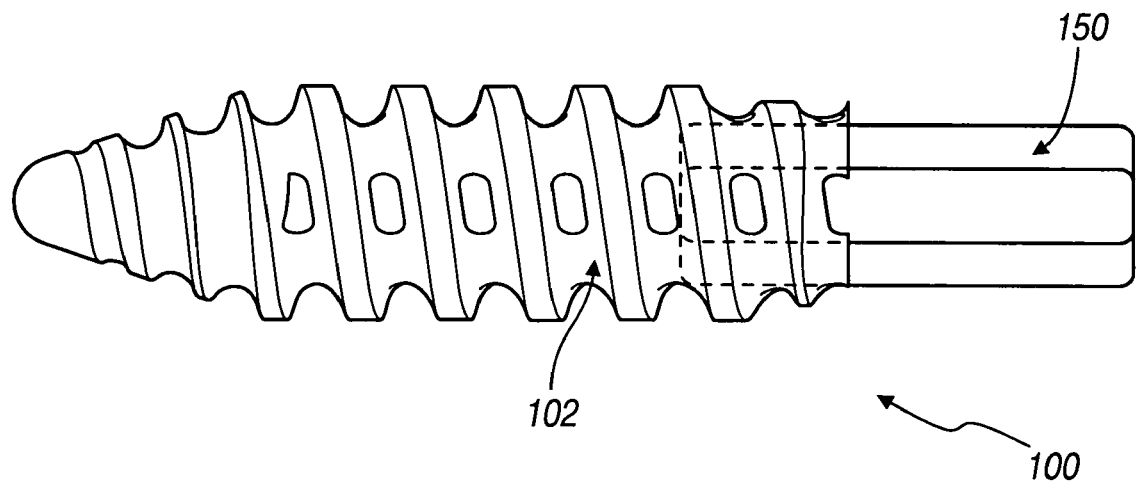
FIG. 1 is a partially assembled perspective view of a fixation device according to the present teachings.

Referring to FIG. 1, an exemplary fixation device 100 according to the present teachings includes a cannulated anchor 102 and a plug 150 that can be received in the anchor 102. FIGS. 2-5 illustrate exemplary anchors 102 and plugs 150. The cannulated anchor 102 includes a cylindrical portion 106 and a tapered tip portion 104. The anchor 102 can be threaded. The cylindrical portion 106 can have threads 114 with pitch $p_1$, and the tapered tip portion 104 can have threads 110 with pitch $p_2$, where $p_1$ is greater than $p_2$. For an exemplary 30 mm long anchor, for example, $p_1$ can be about 2.2 mm and $p_2$ about 1.8 mm, although other values can be used for these dimensions. The threads 114, 110 of both portions 106, 104 can have "blunt" edges that are herein defined as non-cutting edges 108. The small pitch $p_1$ of the tapered tip portion 104 facilitates the insertion of the anchor 102 using only non-cutting edges 108 and avoiding the need for sharp or cutting edges.

Figure 8:
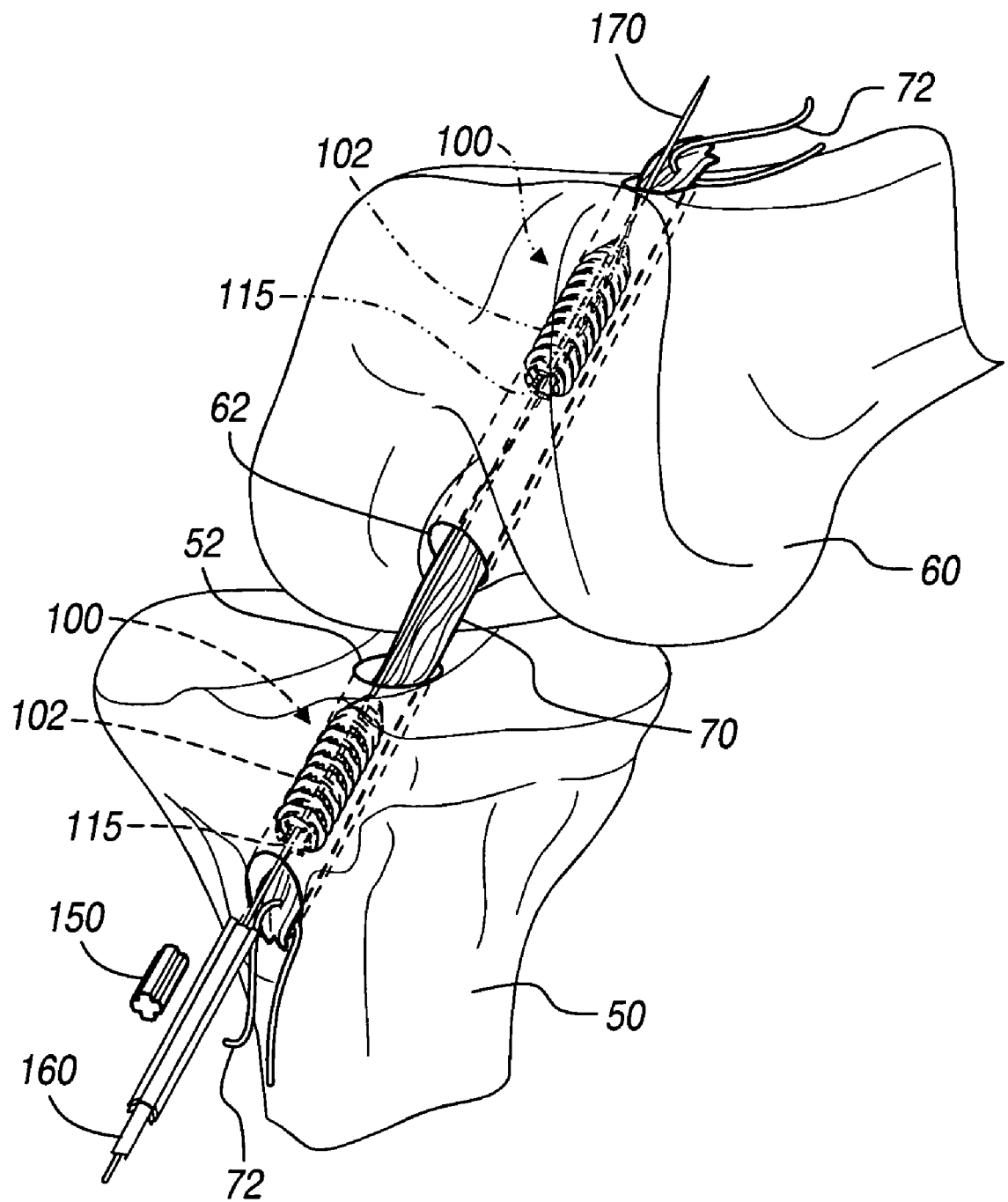
FIG. 8 is an environmental view of a fixation device according to the present teachings.

Referring to FIG. 8, the shape of the tapered tip portion 104 together with the smaller pitch threads 110 facilitates the insertion of the anchor 102 into a bone tunnel 62 to wedge a ligament or graft 70 against the wall of the tunnel 62 by pushing apart, without cutting into, surrounding tissues. The threads 114 of the cylindrical portion 106 also push apart, without cutting into, surrounding tissue, and being of different pitch $p_1$ that is greater than the pitch $p_2$ of the threads 110 of the tapered tip portion 104, do not follow any paths that may be opened by the pushing apart action of the threads 110 of the tapered tip portion 104. The anchor 102 can be made any biocompatible material, including metal, such as titanium, for example. The anchor 102 can also be made of bioabsorbable material, such as Lactosorb® from Biomet, Inc., Warsaw, Ind., for example.

Figure 3:
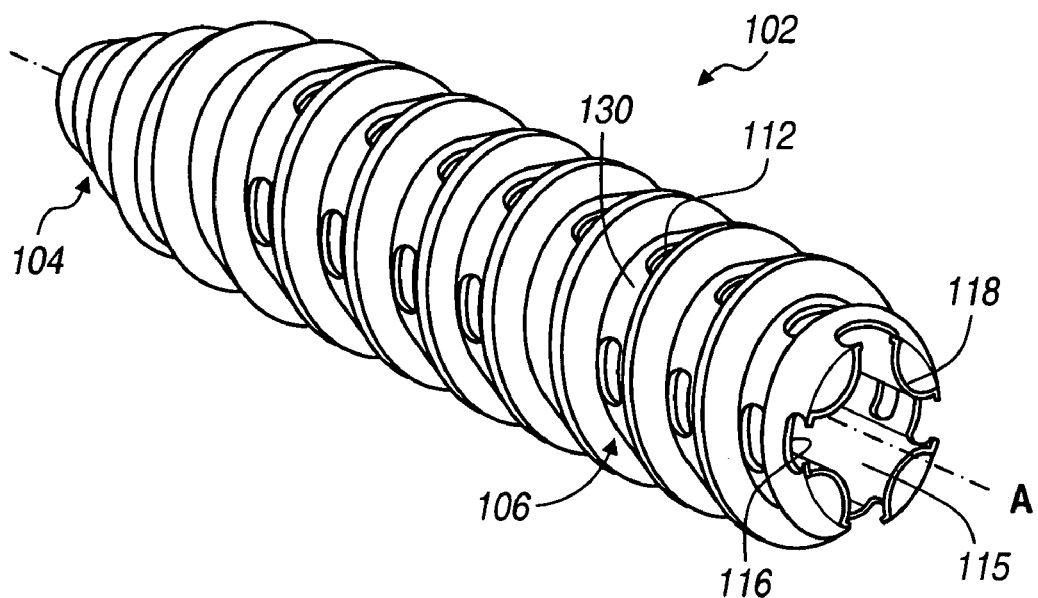
FIG. 3 is a perspective view of an anchor for a fixation device according to the present teachings.
Figure 5:
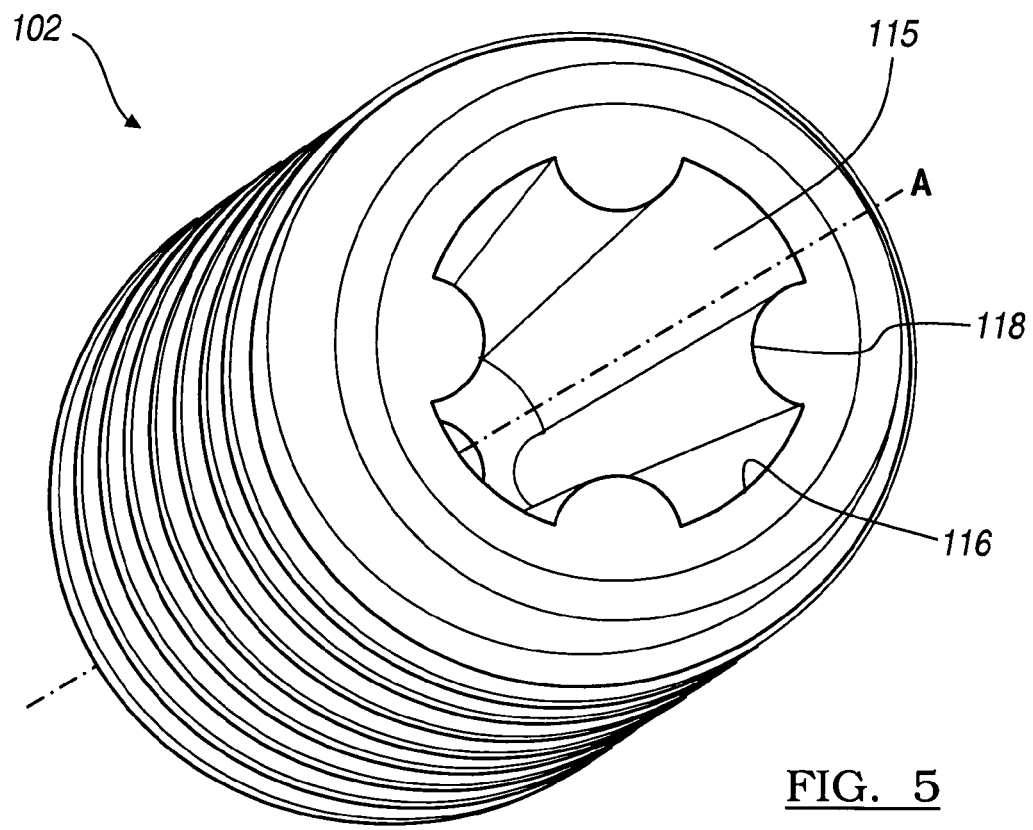
FIG. 5 is a perspective view of an anchor for a fixation device according to the present teachings.
Figure 6:
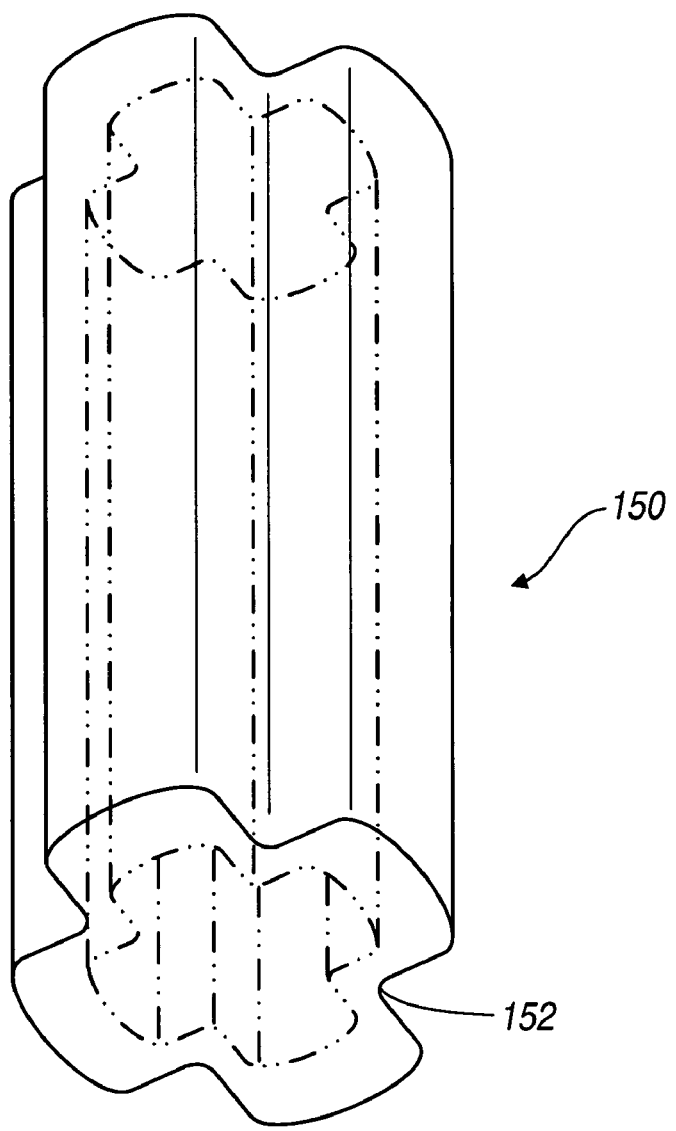
FIG. 6 is a perspective view of a plug for a fixation device according to the present teachings.

Referring to FIGS. 3, 5 and 6, the cannulated body of the anchor 102 defines a longitudinal passage 115 that extends throughout the entire body of the anchor 102 along a longitudinal center axis "A". A plug-receiving portion 116 of the longitudinal passage 115 extends along the cylindrical portion 106 of the anchor and can have an enlarged opening of a shape such as a cruciate shape defined by four longitudinal ribs 118, or any other shape, such as a fingered shape, a hexagonal, pentagonal, triangular or other polygonal shape. The plug 150 has a shape that is complementary to the shape of the plug-receiving portion 116. For example, for the cruciate shape the plug 150 can have grooves 152 shaped for mating with the ribs 118 when the plug 150 is inserted into the passage 115. The plug 150 can be made of osteoinductive and/or osteoconductive material to promote bone growth through the anchor 102. The material of the plug 150 can be, for example, calcium phosphate, calcium sulfate, tricalcium phosphate, allograft bone, autograft bone, combinations thereof, etc. The plug 150 can be cannulated.

Figure 2:
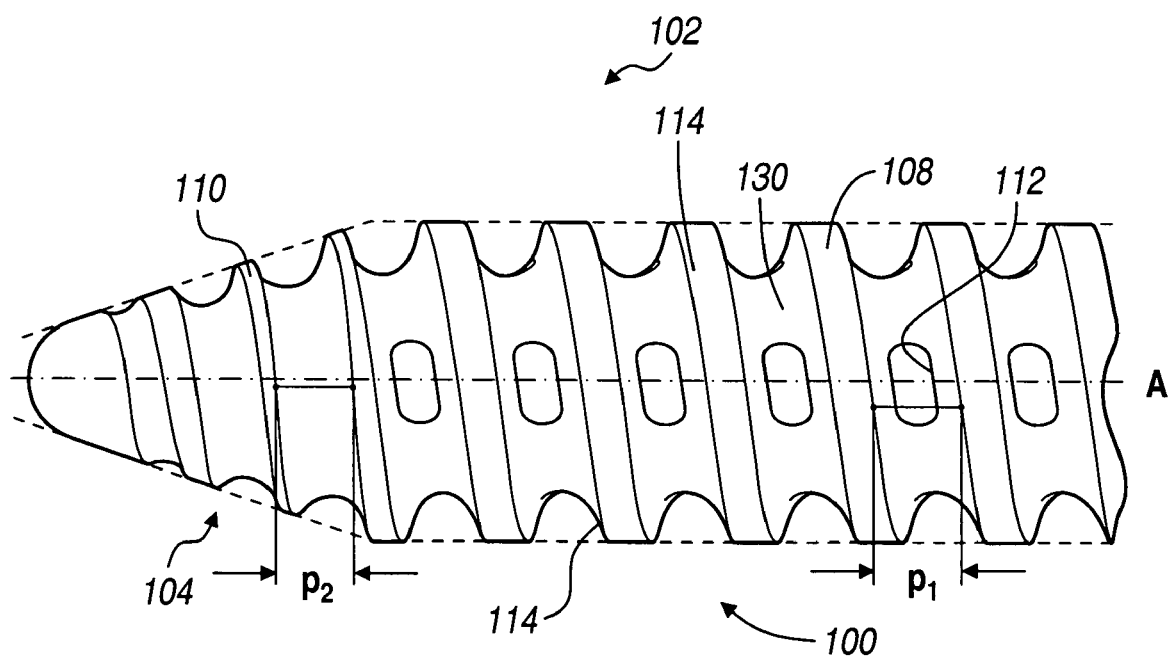
FIG. 2 is a perspective view of an anchor for a fixation device according to the present teachings.
Figure 4:
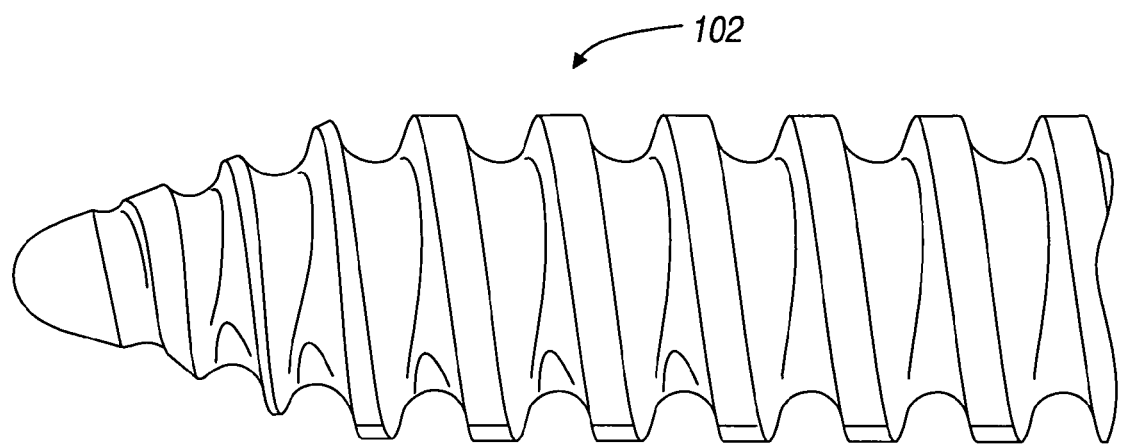
FIG. 4 is a perspective view of an anchor for a fixation device according to the present teachings.

Referring to FIGS. 4 and 5, the cylindrical portion 106 of the anchor can be solid, without any apertures. Referring to FIGS. 2 and 3, the outer surface of the cylindrical portion 106 of the anchor 102 between the threads 114 can also include apertures 112. The apertures 112 can be formed, for example, by cutting through from the inside to the outside the outer surface 130 of the anchor 102 between the threads 114, using a cutting instrument that can be received in the anchor 102, although other cutting methods can also be used. The apertures 112 are, therefore, confined in the direction of the longitudinal axis A between adjacent threads 114 of the cylindrical portion 106. The apertures 112 extend substantially parallel to the threads 114 in the regions between adjacent ribs 118. The size of the apertures 112 can be selected to occupy only a portion of the outer surface 130 between the threads 114, as illustrated in FIG. 2.

Referring to FIG. 3, the size of the apertures 112 can also be selected to occupy the entire portion of the outer surface 130 between the threads 114 and the ribs 118. In this respect, the structural integrity of the cylindrical portion 106 of the anchor 102 is provided by the threads 114 and the ribs 118, with no material therebetween. The apertures 112 facilitate bone ingrowth or outgrowth through the anchor 102 and can also be used to distribute a biologic material, including osteoinductive/osteoconductive material, such as calcium phosphate, platelet concentrates, fibrin, etc., which may be injected through the passage 115. The plug 150, in addition to providing bone growth promoting benefits, closes the longitudinal passage 115 and can prevent such material from draining out.

Figure 3A:
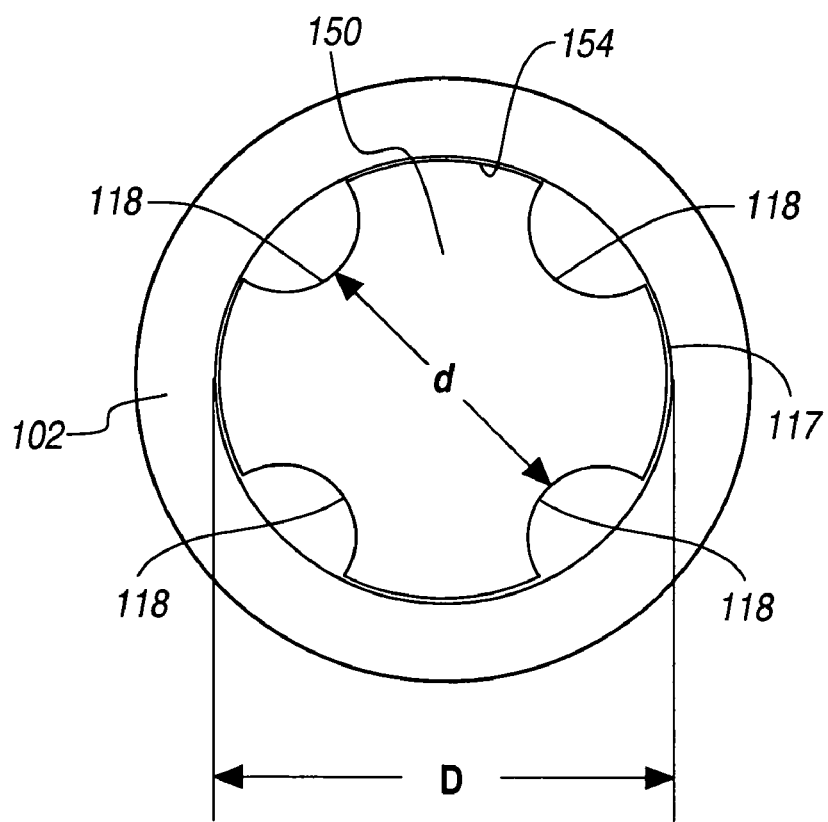
FIG. 3A is a cross-sectional view of a cannulated anchor with a plug inserted therein for a fixation device according to the present teachings.

Referring to FIG. 3A, the outer surface 154 of the plug 150 is shaped to extend outward beyond a minor diameter "d" defined by the ribs 118. The outer surface 154 of the plug mates with interior surface 117 of the anchor 102 at a major diameter "D" at which the apertures 112 are formed, such that portions of the plug 150 can contact tissue through the apertures 112 when the anchor 102 is implanted, thereby promoting tissue growth and better tissue attachment.

Figure 7:
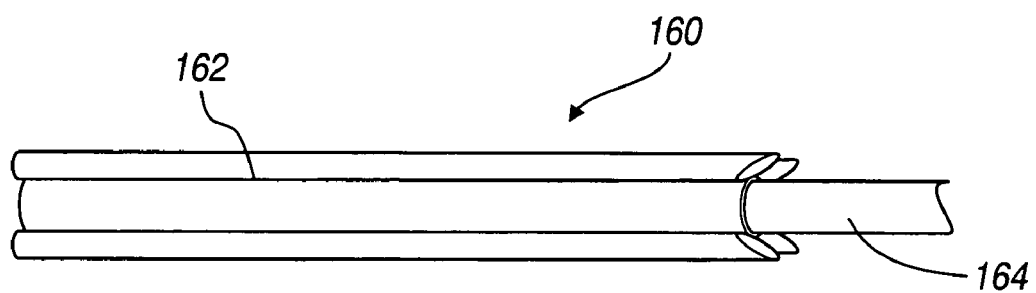
FIG. 7 is a perspective view of a driver for use with a fixation device according to the present teachings.

Referring to FIG. 7, a driver 160 can be used to rotate the anchor 102 and facilitate its insertion. The driver 160 includes a handle portion 164 and a suitably shaped portion 162 for engaging the plug-receiving portion 116 of the passage 115 of the anchor 102. Alternatively, the plug 150 can be pre-inserted into the anchor 102 and the driver 160 can engage the cannulated plug 150. The driver 160 can also be cannulated. The driver 160 can have a cruciate shape or any other shape that can engage the plug-receiving portion 116.

Referring to FIG. 8, an exemplary, but not limiting, use of the fixation device 100 is illustrated in the context of arthroscopic knee surgery. A ligament or graft 70 passes through a tibial tunnel 52 and a femoral tunnel 62 and is fixed in the tibia 50 and femur 60 with sutures 72. The fixation device 100 can be implanted in the tibial tunnel 52 or in the femoral tunnel 62, or two fixation devices 100 can be implanted, one in each tunnel 52, 62. A guide wire 170 is inserted between the wall of tibial tunnel 52/femoral tunnel 62 and the graft 170 to guide the anchor 102 of the fixation device 100, as needed. The anchor 102 is passed over the guide wire 170 and wedged between the graft 170 and the tibial tunnel 52/femoral tunnel 62 by rotation using the cannulated driver 160. The guide wire 170 is then removed. The passage 115 is then closed by inserting the plug 150.

Osteoinductive/conductive material can be optionally injected through the passage 115 of the anchor 102 using, for example, the cannulated driver 160, a syringe, a pump or other suitable delivery device before inserting the plug 150.

While particular embodiments have been described in the specification and illustrated in the drawings, it will be understood by those skilled in the art that various changes may be made and equivalents may be substituted for elements thereof without departing from the scope of the invention as defined in the claims. In addition, many modifications may be made to adapt a particular situation or material to the present teachings without departing from the essential scope thereof. Therefore, it is intended that the present teachings are not to be limited to the particular embodiments illustrated by the drawings and described in the specification, but that the present teachings will include any embodiments falling within the foregoing description and the appended claims.

What is claimed is:

1. A fixation device for securing tissue to a bone, the fixation device comprising:
   an implantable anchor having a body extending between a first end and a second end, the body having an outer surface with a cylindrical portion and a tapered tip portion the body being externally threaded from the first end to the second end, the threads having blunt edges, the cylindrical portion having a length and defining an inner longitudinal passage having an inner surface of a cruciate shape along the length of the cylindrical portion, the longitudinal passage including four inner longitudinal ribs; and
   separate elongated plug having an outer surface of cruciate shape, the elongated plug including four outer longitudinal grooves, the elongated plug slidably receivable within and mateable with the inner longitudinal passage along the length of the externally threaded cylindrical portion, such that the inner longitudinal ribs of the longitudinal passage are received in the corresponding outer longitudinal grooves of the elongated plug, the elongated plug formed of a material promoting bone growth through the anchor.

2. The fixation device of claim 1, wherein the cylindrical portion has threads with a first pitch and the tapered tip portion has threads with a second pitch, the first pitch being different than the second pitch.

3. The fixation device of claim 2, wherein the first pitch is greater than the second pitch.

4. The fixation device of claim 1, wherein the plug comprises osteoinductive/osteoconductive material.

5. The fixation device of claim 1, wherein the plug is made of material selected from the group consisting of calcium phosphate, calcium sulfate, tricalcium phosphate, allograft bone, autograft bone and combinations thereof.

6. The fixation device of claim 1, wherein the anchor is made of biocompatible material.

7. The fixation device of claim 1 in combination with a driver.

8. The fixation device of claim 7, wherein the driver has a portion shaped for engaging and mating with the longitudinal passage of the anchor.

9. The fixation device of claim 8, wherein the driver is cannulated.

10. The fixation device of claim 1, wherein the cylindrical portion of the outer surface includes a plurality of apertures communicating with the longitudinal passage, the apertures formed between the threads of the cylindrical portion and between adjacent longitudinal ribs of the longitudinal passage.

11. The fixation device of claim 10, wherein the apertures are substantially parallel to the threads of the cylindrical portion and are confined therebetween.

12. The fixation device of claim 1, wherein the longitudinal grooves and the longitudinal ribs have curved mating surfaces.

13. A fixation device for securing tissue to a bone, the fixation device comprising:
   an implantable anchor extending from a first end to a second end and having a cannulated body, the cannulated body having an outer surface with an externally threaded cylindrical portion and a tapered tip portion, the outer surface having threads with blunt edges, the threads extending from the first end to the second end, the externally threaded cylindrical portion having a length and defining an inner longitudinal passage having an inner surface of a cruciate shape alone the length of the inner longitudinal passage, the inner longitudinal passage including four inner longitudinal ribs, the externally threaded cylindrical portion of the outer surface including a plurality of apertures therethrough, the apertures communicating with the inner longitudinal passage, the apertures formed between the threads and between adjacent inner longitudinal ribs of the passage; and separate elongated plug having an outer surface of cruciate shape, the elongated plug including four outer longitudinal grooves, the elongated plug slidably receivable within and mateable with the inner longitudinal passage along the length of the externally threaded cylindrical portion, such that the inner longitudinal ribs of the inner longitudinal passage are matingly received in the corresponding outer longitudinal grooves of the elongated plug, wherein the outer longitudinal grooves and the inner longitudinal ribs have curved mating surfaces, and the elongated plug is formed of calcium phosphate material for promoting bone growth through the anchor.

\* \* \* \* \*

UNITED STATES PATENT AND TRADEMARK OFFICE
CERTIFICATE OF CORRECTION

PATENT NO. : 7,608,098 B1
APPLICATION NO. : 10/984624
DATED : October 27, 2009
INVENTOR(S) : Kevin T. Stone et al.

Page 1 of 1

It is certified that error appears in the above-identified patent and that said Letters Patent is hereby corrected as shown below:

Column 4
Line 6-7, insert --,-- after "portion".

Column 4
Line 14, insert --a-- before "separate".

Column 4
Line 67, "alone" should be --along--.

Column 5
Line 8, insert --a-- before "separate".

Signed and Sealed this

Twenty-ninth Day of December, 2009

David J. Kappos
*Director of the United States Patent and Trademark Office*